United States Patent [19]
Tanimoto et al.

[11] Patent Number: 5,879,942
[45] Date of Patent: Mar. 9, 1999

[54] PROCESSING ENZYME FOR POLYPEPTIDE

[75] Inventors: Tadao Tanimoto; Masashi Kurimoto, both of Okayama, Japan

[73] Assignee: Kabushiki Kaisha Hayashibara Seibutsu Kagaku Kenkyujo, Okayama, Japan

[21] Appl. No.: 896,605

[22] Filed: Jul. 18, 1997

[30]     Foreign Application Priority Data

Jul. 19, 1996  [JP]  Japan .................................. 8-207691
May 30, 1997  [JP]  Japan .................................. 9-156062

[51] Int. Cl.⁶ ........................................................ C12N 9/64
[52] U.S. Cl. ............................................ 435/226; 435/219
[58] Field of Search ...................................... 435/226, 219

[56]              References Cited
              U.S. PATENT DOCUMENTS 4,276,282   6/1981   Sugimoto et al. ...................... 424/85

FOREIGN PATENT DOCUMENTS 0 692 536    1/1995   European Pat. Off. .
0 712 931    5/1996   European Pat. Off. .
56-054158   12/1981   Japan .
08-027189    1/1996   Japan .
08-193098    7/1996   Japan .
08-231598    9/1996   Japan .

OTHER PUBLICATIONS

Micallef, M.J., et. al (1996) Eur. Jr. Immunol. 26, 1647–1651.

Okamura, H., et. al. (1995) Infect. Immunol. 63(10), 3966–3972.

Okamura, H., et. al. (1995) Nature 378, 88–91.

Minowada, Jun., "Leukemia cell lines." Cancer Rev., vol. 10, pp. 1–18 (1988).

Kuroki, Toshio ed. et al., Jikken–Igaku–Bessatsu–Saibo–Kogaku–Handbook, (1992).

Yokota, Takashi ed. et al., Jikken–Igaku–Bessatsu–Biomaterial Series 3, "Genetic Cloning Experimental Method" (1993).

Laemmli, U.K., "Cleavage of structural proteins during the assembly of the head of bacteriophage T4.", Nature, vol. 227, pp. 680–685 (1970).

Hay, Robert ed. et al., "Catalogue of cell lines & hybridomas.", 6th Ed. (1988).

Hay, Robert ed. et al., "ATCC Cell lines and hybridomas.", 8th Ed. (1994).

Hay, Robert ed. et al., "American type culture collection catalogue of cell lines and hybridomas.", 6th Ed. (1988).

*Primary Examiner*—Charles L. Patterson, Jr.
*Attorney, Agent, or Firm*—Browdy and Neimark

[57]              ABSTRACT

Disclosed are an enzyme or a protein which converts a precursor of a polypeptide that induces IFN-γ production in an immunocompetent cell into the active form, a process for producing the enzyme comprising proliferating a cell which produces the enzyme and collecting the produced enzyme from the proliferated cells, and a method for converting the precursor into the active form.

25 Claims, 1 Drawing Sheet

PROCESSING ENZYME FOR POLYPEPTIDE

BACKGROUND OF THE INVENTION

1. Field of the Invention

The present invention relates to a processing enzyme for a polypeptide, more particularly, to an enzyme which converts a precursor of a polypeptide that induces interferon-γ (hereinafter abbreviated as "IFN-γ") production in immunocompetent cells into the active form.

2. Description of the Prior Art

The present inventors succeeded in isolating a polypeptide which induces IFN-γ production in immunocompetent cells and a cDNA encoding the polypeptide, and disclosed them in Japanese Patent Kokai Nos.27,198/96 and 193,098/96.

The polypeptide is featured in inducing the production of IFN-γ as a useful biologically active substance, enhancing the cytotoxicity by killer cells, and inducing the formation of killer cells; it can be expected for use as anti-virus agents, antiseptics, antitumor agents and anti-immunopathy agents.

It is said that, in human cells, polypeptides formed by gene expression may be processed by intracellular enzymes to partially digest the polypeptides and add sugar chains thereunto.

Polypeptides to be satisfactorily incorporated into pharmaceuticals may be those which received processings similarly as in human cells; such cells have a demerit that they less produce the present polypeptide as disclosed in Japanese Patent Application No.269,105/96. The present inventors' energetic study revealed that the polypeptide usually exists in human cells in the form of a precursor with a molecular weight of about 24,000 daltons and no biological activity. Although it is not restricted to the polypeptide, it is known that most cytokines are usually produced as precursors with no biological activity, and then processed by intracellular enzymes to be converted into their active forms.

SUMMARY OF THE INVENTION

In view of the foregoing, the first object of the present invention is to provide an enzyme which acts on a precursor of a polypeptide that induces IFN-γ production in immunocompetent cells to convert the precursor into the active form that induces IFN-γ production in immunocompetent cells.

The second object of the present invention is to provide a method for producing the enzyme.

The third object of the present invention is to provide a method for converting the precursor into the active form that induces IFN-γ production in immunocompetent cells.

The present inventors energetically studied to solve the object and found that an enzyme, isolated from a human cell line, acts on a precursor of the polypeptide to convert the precursor into the active form that induces IFN-γ production in immunocompetent cells. They confirmed that the enzyme can be produced from artificially proliferated cells, particularly, human hematopoietic cells, and accomplished this invention.

The first object of the present invention is solved by an enzyme which converts a precursor of a polypeptide which induces IFN-γ production in immunocompetent cells into the active form.

The second object of the present invention is solved by a process for producing the enzyme comprising culturing cells which produce the enzyme in nutrient culture media, and collecting the produced enzyme from the resultant cultures.

The third object of the present invention is solved by a conversion method for polypeptide comprising a step of contacting the enzyme with the precursor to convert it into the active form.

BRIEF DESCRIPTION OF THE ACCOMPANYING DRAWINGS

Figure 1:
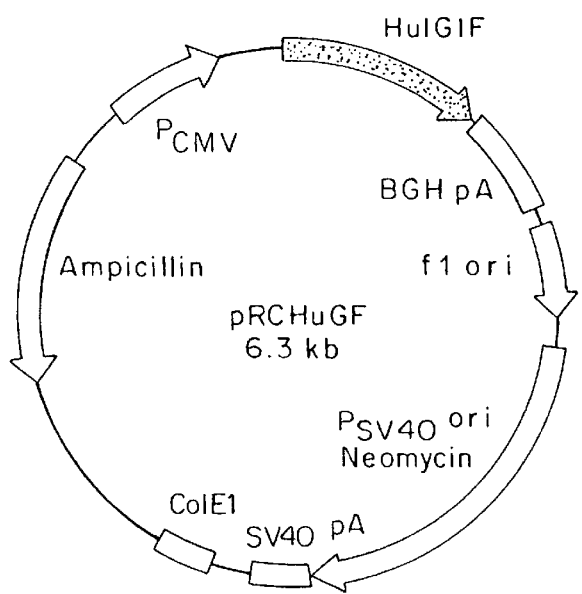
FIG. 1 is a structure of the recombinant DNA pRCHuGF containing cDNA which encodes a precursor of the polypeptide according to the present invention.

In the figures, "PCMV" means a cytomegalovirus promotor, and "HuIGIF" means a cDNA encoding a precursor of the polypeptide according to the present invention.

DETAILED DESCRIPTION OF THE INVENTION

As described above, the present invention was made based on the finding of an enzyme which converts a precursor of a polypeptide that induces IFN-γ production in immunocompetent cells into the active form. The precursor as referred to in the present invention has a molecular weight of about 24,000 daltons on SDS-polyacrylamide gel electrophoresis (SDS-PAGE) in the presence of a reducing agent, and exists, for example, in cells which inherently produce the polypeptide and in mammalian host cells transformed by introducing a DNA, e.g., a DNA with the nucleotide sequence of SEQ ID NO:5, containing a region which encodes the polypeptide. Such a precursor contains a part of or the whole of the amino acid sequence of SEQ ID NO:1 at the N-terminal region, and in whole, contains either the whole amino acid sequence of SEQ ID NO:2 (where the symbol "Xaa" is "isoleucine" or "threonine") and has a molecular weight of 18,000–19,500 daltons on SDS-PAGE in the presence of a reducing agent.

The enzyme as referred to in the present invention includes any natural and artificially produced ones as long as they produce the active form that induces IFN-γ production in immunocompetent cells without restricting to specific origins and sources. The present enzyme obtainable from a human hematopoietic cell generally has the following physicochemical properties:

(1) Molecular weight
   Exhibiting molecular weights of about 25,000 and about 10,000 daltons on SDS-PAGE;

(2) Partial amino acid sequence
   Having an amino acid sequence selected from the group consisting of SEQ ID NO:4, where the symbol "Xaa" is "asparagine" or "aspartic acid", and SEQ ID NO:5; and (3) Inhibitory agent
   Being inhibited by acetyl-L-tyrosyl-L-varyl-L-alanyl-L-aspart-1-al (hereinafter abbreviated as "Ac-YVAD-CHO") and iodoacetamide.

The enzyme can be produced by the present method using cells as the sources. Any natural cells and artificially obtained cell lines and transformants from the natural cells can be used as the sources. These cell lines and transformants are especially useful to practice this invention. The former can be obtained by establishing from human hematopoietic cells such as lymphoblasts, lymphomas, monoblasts, monocytes, myeloblasts, myelocytes, granulocytes and macrophages; epidermal cells including tumor cells such as submaxillary adenocancroid, lung cancer, large intestinal cancer, and colon cancer; neuroblasts and interstitial cells. Examples of each cell lines are HBL-38 cells, HL-60 cells (ATCC CCL240), K-562 cells (ATCC CCL243), KG-1 cells (ATCC CCL246), Mo cells (ATCC CRL8066), THP-1 cells (ATCC TIB202), and U-937 cells (ATCC CRL1593.2), as described by Jun MINOWADA in *Cancer Review*, Vol.10, pp.1–18 (1988), which are derived from leukemias and lymphomas including myelocytic leukemia, promyelocytic leukemia, monocytic leukemia, adult T-cell leukemia, hairy cell leukemia, and mutants thereof. Because all these cell lines easily proliferate and produce the present polypeptide in a relatively-high yield, they can be advantageously used in the present invention. Particularly, human myelomonocytic cell lines such as HBL-38 cells, HL-60 cells, KG-1 cells, THP-1 cells and U-937 cells extremely-highly produce the present polypeptide. Thus, they can be advantageously used in the present invention.

The aforesaid transformants of cell lines can be obtained by introducing a DNA, which encodes the present polypeptide obtained from the above cell lines, into appropriate mammalian host cells. Examples of such host cells include epidermal-, interstitial-, neuroblast-, hematopoietic-cell lines, which are derived from humans, monkeys, mice and hamsters and used conventionally as hosts, such as 3T3 cells (ATCC CCL92), C1271 cells (ATCC CRL1616), CHO K1 cells (ATCC CCL61), CV-1 cells (ATCC CCL70), COS-1 cells (ATCC CCL70), HeLa cells (ATCC CCL2), MOP-8 cells (ATCC CRL1709) and mutants thereof. Methods to introduce a DNA encoding the enzyme into the host cells include conventional DEAE-dextran method, phosphoric acid-calcium method, electroporation, lipofection, microinjection, and virus-infection method using retrovirus, Adenovirus, herpesvirus and vaccinia virus. From the transformants, clones which produce the enzyme can be selected by colony hybridization method in a manner that the transformants were cultured in nutrient culture media and the desired clones observed with the enzyme production were selected. Recombinant DNA technologies using mammalian host cells are disclosed in detail in *"Jikken-Igaku-Bessatsu-Saibo-Kogaku-Handbook"*, edited by Toshio KUROKI, Masaru TANIGUCHI and Mitsuo OSHIMURA (1992) and in *"Jikken-Igaku-Bessatsu-Biomaterial Series 3, Genetic Cloning experimental Method"*, edited by Takashi YOKOTA and Kenichi ARAI, edited by Yodo Publisher, Tokyo, Japan (1993).

The process according to the present invention comprises proliferating the above cell lines and collecting the desired enzyme from the proliferated cells. Referring to the methods for proliferating the cell lines, they are not specifically restricted and include those which are in vivo and in vitro proliferation methods generally used in this field. The in vitro proliferation methods mean those which proliferate cells in nutrient culture media such as conventional ones used for culturing mammalian cells. Generally, the media comprise buffer water as a base and inorganic ions such as sodium, potassium, calcium, phosphorus and chloride ions, and others such as trace elements, carbon sources, nitrogen sources, amino acids and vitamins, which are required depending on cells' metabolizability. If necessary, sera, hormones, cell growth factors, and cell adherent factors can be incorporated into the media. Examples of such media include 199, DMEM, Ham's F12, IMDM medium, MCDB104, MCDB153, MEM, RD, RITC80-7, RPMI 1630, RPMI 1640 and WAJC404 media. Into these media are inoculated the cell lines in a cell concentration of about $1 \times 10^4$–$1 \times 10^7$ cells/ml, preferably, about $1 \times 10^5$–$1 \times 10^6$ cells/ml, and cultured in a suspension or monolayer culture at about 37– C. for 1–7 days, preferably, 2–4 days while replacing the media with fresh ones, if desired.

The in vivo proliferation methods using non-human warm-blooded animals comprise injecting generally antithymus antibodies from rabbits into new born rodents such as mice, nude mice, rats, nude rats, guinea pigs and hamsters to reduce immunoreactions, and then either injecting subcutaneously or intraperitoneally into each animal about $1 \times 10^5$–$1 \times 10^8$ cells of those which can produce the present enzyme, or placing the human cells in diffusion chambers, embedded in the animals, in which the animals' nutrient body fluids can circulate, and then feeding the animals for about 2–10 weeks in a conventional manner. During the feeding, the transplanted cells proliferate while receiving the animals' body fluids. Thereafter, the proliferated cells are collected in the form of tumor masses, ascites or cell suspensions in the body fluids or media, and if necessary, the collected cells are dispersed in and washed with appropriate media, followed by recovering the desired enzyme. Compared with the in vitro proliferation methods, the in vivo methods provide desired amounts of cells in a lower cost, labor and time as a merit. For example, Japanese Patent Publication No.54,158/81 discloses the in vivo proliferation methods in detail.

The enzyme can be collected from the proliferated cells by either treating with ultrasonics the cells separated from the cultures or the intact cultures, or soaking the cells in hypotonic media for cell disruption, and then treating the resulting cell debris or mixtures of such cell debris and culture supernatants with conventional methods used for purifying enzymes in this field such as salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing used for purifying enzymes in this field. Two or more of these purification methods can be used in combination depending on purposes. Specifically, immunoaffinity chromatography using monoclonal antibodies specific to the present enzyme yields a relatively-high purity enzyme in the lowest cost and labor. Depending on the types of cells and culture conditions, the enzyme may be obtained from the culture supernatants when the produced enzyme is extracellularly secreted during the cell proliferation.

In the present invention, the activity of the enzyme according to the present invention is assayed as follows and expressed with units: 395 $\mu$l of 25 mM Hepes buffer (pH 7.5) containing 10 w/v % sucrose, 2 mM dithiothreitol and 0.1 w/v % 3-[(3-cholamidopropyl)dimethylammonio]-1-propanesulfonic acid (hereinafter abbreviated as "CHAPS") was placed in a container, and admixed with 100 $\mu$l of a testing enzyme solution and 5 $\mu$l of 10 mM N-(N-acetyl-tyrosyl)-valinyl-alanyl-aspartic acid-7-amino-4-methylcoumarinamide, followed by the incubation at 30° C. for one hour. During the reaction, the content of 7-amino-4-methylcoumarin released as the reaction proceeded was checked by monitoring with a fluorometry the intensity of a fluorescent at a wavelength of 460 nm emitted by the excitation by a light with a wavelength of 355 nm. One unit activity of the enzyme is defined as the amount which releases one pmole of 7-amino-4-methylcoumarin per min under these reaction conditions.

The present invention provides a method for converting a precursor of the polypeptide into the active form by contacting the enzyme with the precursor: For example, the present enzyme, once isolated by the above methods, is contacted with the precursor, or both a DNA encoding the enzyme and a DNA containing a nucleotide region encoding the precursor are incorporated into appropriate host cells to express both the DNAs. In the former case, either cells which produce the precursor of the polypeptide or those which acquired an ability to produce the precursor by transformation are cultured. The enzyme obtained by the above methods is contacted with the resulting cultures or added to the cells separated or not separated from the cultures, or if necessary, to cell debris or mixtures obtained after disrupting the cells in such conditions. Sufficient amount of the enzyme to be coexisted or added is an equimolar or lower amount of the precursor, and the mixture is incubated at pHs and temperatures, which allow the enzyme to act on the precursor until it is converted into the active form, particularly, at temperatures of about 4–40° C., preferably, about 37° C., and pHs of about 6–9, preferably, about 7–8. In the latter case, both the DNA encoding the enzyme and a DNA which contains a region encoding the polypeptide are introduced into appropriate mammalian host cells to transform the cells; the resulting transformed cells produce both the desired precursor and enzyme without necessarily requiring the present enzyme. For such transformed cells, they can be only incubated intact at temperatures, which allow the present enzyme to act on the precursor to convert it into the active form, or incubated after being homogenized into cell debris, if necessary.

The resulting cultures containing the active form can be used intact as an IFN-γ inducer, and usually, cells in the cultures are disrupted by ultrasonics, cell lysis enzymes and/or surfactants, followed by separating the polypeptide from the cells and cell debris by filtration, centrifugation, etc., and purifying the separated polypeptide. In the purification, the cultures free of cells or cell debris were purified by conventional purification methods used to purify biologically active substances in this field, for example, salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing. If necessary, two or more of these purification methods can be used in combination. The resulting purified polypeptide can be concentrated and lyophilized into a liquid or solid product to meet their final uses. The monoclonal antibody, as disclosed in Japanese Patent Kokai No.231,598/96 by the same applicant of the present invention, can be advantageously used to purify the polypeptide: For example, affinity chromatography using the monoclonal antibody can yield the desired polypeptide with a relatively-high purity in the lowest cost and labor.

As described above, the active form of the precursor, i.e., an active polypeptide obtained by the present method has an activity of inducing the production of IFN-γ as a useful biologically active substance, enhances the killer cells' cytotoxicities, and induces the killer cells' production. Thus, the polypeptide exerts a strong activity in the treatment and/or the prevention of IFN-γ and/or killer cell-susceptive diseases. Since the active polypeptide obtained by the present method has a strong IFN-γ inducibility, it generally induces a prescribed amount of IFN-γ production with only a relatively-small amount. The active polypeptide does not substantially induce serious side effects even when administered to the body in a relatively-high dose because of its extremely-low toxicity, and has a merit that it smoothly induces a desired amount of IFN-γ production without strictly controlling the dose in actual use. Japanese Patent Application No.28,722/96 by the same applicant of the present invention discloses in detail the uses of the active polypeptide as an agent for susceptive diseases.

The following examples explain the present invention:

EXAMPLE 1

Preparation of Enzyme

New born hamsters were intraperitoneally injected with rabbit antithymus antiserum to lower the immunoreaction, then injected to their dorsal subcutaneous tissues with about $5 \times 10^5$ cells of THP-1 cells (ATCC TIB202) per hamster, and fed for 3 weeks in a conventional manner. Tumor masses, about 15 g weight each, formed subcutaneously in the hamsters, were extracted, then suspended in RPMI 1640 medium (pH 7.4) in a conventional manner and washed to obtain proliferated cells.

The cells were washed with 10-time volumes of an ice-chilled 20 mM Hepes buffer (pH 7.4) containing 1.5 mM magnesium chloride and 0.1 mM ethylenediamine-N,N,N', N'-tetraacetic acid disodium salt, allowed to stand in 3-time volumes of a fresh preparation of the same buffer for 20 min under ice-chilling conditions, and freezed at −20° C. The freezed product was thawed, mixed with one mM phenyl-methylsulfonyl fluoride, one µg/ml of leupeptin and 10 µg/ml of pepstatin A, and then homogenized by a teflon homogenizer. The disrupted cells were centrifuged at 2,000×g for 10 min to obtain a supernatant, and the precipitate was treated again similarly as above and centrifuged to obtain a supernatant which was then pooled with the above supernatant. The pooled supernatant was admixed with ethylenediamine-N,N,N',N'-tetraacetic acid disodium salt to give a concentration of 6 mM, centrifuged at 24,000×g for 20 min to remove cell debris, and further centrifuged at 100,000×g for 60 min to form microsome- and cytosol-fractions, followed by collecting the latter fraction.

To the collected fraction was added ammonium sulfate to give a saturation degree of 40% under ice-chilling conditions, and the mixture was stirred and centrifuged to obtain a supernatant. Ammonium sulfate was further added to the supernatant to give a saturation degree of 80%, stirred and centrifuged to collect the precipitate which was then dissolved in 20 mM Tris-HCl buffer (pH 7.8) containing 5 v/v % glycerol, 0.1 w/v % CHAPS, and 2 mM dithiothreitol. The solution was injected to a dialysis bag and dialyzed against a fresh preparation of the same buffer at 4° C. for 16 hours. The inner solution of the bag was centrifuged to obtain a supernatant which was then fed to a column packed with "DEAE 5PW", a resin for ion-exchange chromatography commercialized by Tosoh Corporation, Tokyo, Japan, which had been equilibrated with a fresh preparation of the same buffer, followed by feeding to the column a linear gradient buffer of sodium chloride increasing from 0M to 0,5M in the same buffer, collecting fractions eluted at sodium chloride concentrations of 0.04–0.09M and pooling the fractions.

The collected fraction was diluted by 1.5-times with 20 mM Hepes buffer (pH 7.4) containing 5 v/v % glycerol, 0.1 w/v % CHAPS and 2 mM dithiothreitol, and the dilution was adjusted to pH 7.4 by the addition of dilute hydrochloric acid, and then fed to a column packed with "S-SEPHAROSE", a gel for ion-exchange chromatography commercialized by Pharmacia LKB Biotechnology AB, Uppsala, Sweden, which had been equilibrated with a fresh preparation of the same buffer. The column was washed with a fresh preparation of the same buffer and fed with a linear gradient buffer of potassium chloride increasing from 0M to 0.5M in the same buffer, followed by collecting fractions eluted at potassium concentrations of about 0.01–0.1M.

The fractions were pooled, dialyzed for 16 hours against 20 mM Hepes buffer (pH 7.4) containing 5 v/v % glycerol, 0.1 w/v % CHAPS, and 2 mM dithiothreitol, and fed to a column of "MONO S", a column for ion-exchange chromatography commercialized by Pharmacia LKB Biotechnology AB, Uppsala, Sweden, which had been equilibrated with a fresh preparation of the same buffer, followed by feeding to the column a fresh preparation of the same buffer containing 0.5M potassium chloride.

Fractions, eluted from the "MONO S" column and had the present enzyme activity, were collected, pooled and concentrated. The concentrate was fed to a column of "SUPERDEX 200", a column for gel chromatography commercialized by Pharmacia LKB Biotechnology AB, Uppsala, Sweden, which had been equilibrated with 20 mM Hepes buffer (pH 7.4) containing 5 v/v % glycerol, 0.1 w/v % CHAPS, and 2 mM dithiothreitol, followed by feeding to the column a fresh preparation of the same buffer, collecting fractions with the present enzyme activity, pooling the fractions, and concentrating the mixture to obtain a one ml solution containing about 9,000 units/ml of the enzyme in a yield of about 45 units per hamster.

EXAMPLE 2

Molecular Weight of Enzyme

A column, packed with 24 ml of "SUPERDEX 75HR", a gel for gel filtration chromatography commercialized by Pharmacia LKB Biotechnology AB, Uppsala, Sweden, was equilibrated with phosphate buffered saline (hereinafter abbreviated as "PBS"), then fed with 200 μl of the enzyme solution in Example 1—1, and fed with a fresh PBS at a flow rate of 0.5 ml/min while monitoring the enzyme activity in the eluate. In PBS were dissolved, as molecular markers for gel filtration chromatography, adequate amounts of calf serum albumin with a molecular weight of 67,000 daltons, ovalbumin with a molecular weight of 43.000 daltons, chymotrypsinogen A with a molecular weight of 25,000 daltons, and ribonuclease A with a molecular weight of 13,700 daltons, and the solution was similarly treated as in the assay for the enzyme solution except that the protein concentration in the eluate was monitored by the absorption degree with respect to the wavelength at 280 nm without monitoring the enzyme. Based on the chromatogram of the enzyme and the eluted positions of the molecular makers, the present enzyme was calculated to have a molecular weight of about 30,000 daltons on gel filtration chromatography.

The eluate from the "SUPERDEX 75HP" containing the present enzyme was concentrated and, in accordance with the method in U. K. Lemuli in *"Nature"*, Vol.227, pp.680–685 (1970), electrophoresed in SDS-polyacrylamide gel in the presence of 2 w/v % dithiothreitol as a reducing agent. Using the anti-human ICE-p20 antibody and the antihuman ICE-p10 antibody commercialized by Santa Cruz Biotechnology, Inc., California, USA, the gel was immunostained in an usual manner and colored by "ELC KIT", a product of Amersham Corp., Div. Amersham International, Arlington Heights, USA., to detect two single protein bands at positions corresponding to the molecular weights of about 25,000 and about 10,000 daltons. The molecular markers used in this assay were calf serum albumin with a molecular weight of 67,000 daltons, ovalbumin with a molecular weight of 45,000 daltons, carbonic acid anhydrase with a molecular weight of 30,000 daltons, soy bean trypsin inhibitor with a molecular weight of 20,100 daltons, and α-lactalbumin with a molecular weight of 14,400 daltons.

EXAMPLE 3

Partial Amino Acid Sequence of Enzyme

The enzyme solution containing the present enzyme obtained in Example 1 was dialyzed against 20 mM Hepes buffer (pH 7.4) containing 5 v/v % glycerol and 2 mM dithiothreitol, and concentrated by a centrifugal condenser. The concentrate was in a conventional manner separated on SDS-PAGE using a gel concentration of 15 w/v % and 2 w/v % dithiothreitol as a reducing agent, and the separated proteins were transferred to a difluoride polyvinyl membrane and colored with Coomassie Brilliant Blue, followed by cutting bands corresponding to the molecular weights of about 25,000 and about 10,000 daltons.

Protein components were respectively extracted from the cut gels in a conventional manner, and analyzed for amino acid sequence at the N-terminal region on "MODEL 473A", a protein sequencer commercialized by Applied Biosystems, Inc., Foster City, USA, revealing that the component extracted from the band with a molecular weight of about 25,000 daltons had as a partial amino acid sequence the amino acid sequence of SEQ ID NO:4 where the symbol "Xaa" is "asparagine" or "aspartic acid", while the component extracted from the band with a molecular weight of about 10,000 daltons had the amino acid sequence of SEQ ID NO:5 at the N-terminal region. The data indicates that the present enzyme contains 2 types of subunits with different molecular weights.

EXAMPLE 4-1

Preparation of Precursor

In 0.5-ml of a reaction tube were placed 10 μl of 10×PCR buffer, one μl of 2.5 Mm dNTP, 0.5 μl of a 5 units/μl Taq DNA polymerase solution, and one ng of the recombinant DNA PHIGIF disclosed in Japanese Patent Kokai No.193, 098/96 by the same applicant of the present invention. To the mixture were added oligonucleotides with nucleotide sequences of 5'-AAGGCC AGTGTGCTGGGCCTGGACAGTCAGCAAGG-3'(SEQ ID No:8) and 5'-ACAGCCAGTGTGATGGCTAGTCTT CGTTTTGAACAG-3'(SEQ ID NO:9, which were chemically synthesized based on the nucleotide sequence of SEQ ID NO:7 for a cDNA containing a region encoding the polypeptide, in an amount of 20 pmole each, and volumed up to 100 μl with sterilized distilled water. The resulting mixture was in a conventional manner incubated 30 cycles in a sequential manner at 94° C. for one min, 60° C. for one min, and at 72° C. for one min to effect PCR reaction. "TAKARA PCR AMPLIFICATION KIT" commercialized by Takara Shuzo Co., Ltd., Otsu, Shiga, Japan, was used as a reagent for the PCR reaction.

The reaction product was in a conventional manner cleaved with a restriction enzyme, Bst XI, and 0.1 μg of the resulting DNA fragment with about 800 base pairs (bp) was placed in a container, dissolved in an adequate amount of sterilized distilled water, mixed with 10 ng of "pRc/CMV", a plasmid vector commercialized by Invitrogen BV, NV Leek, Netherlands, which had been cleaved with a restriction enzyme, Bst XI, and adequate amounts of 10×ligation buffer and T4 ligase, mixed with 10 mM ATP up to give a final concentration of one mM, followed by incubating the mixture at 16° C. for 18 hours to introduce the DNA fragment into the plasmid vector pRC/CMV. The recombinant DNA thus obtained was introduced into an *Escherichia coli* JM109 strain to obtain a transformant which was then inoculated to L-broth (pH 7.2) containing 50 µg/ml of ampicillin and incubated at 37° C. for 18 hours. Thereafter, the proliferated cells were collected from the culture and treated with alkali-SDS method to extract a recombinant DNA. The recombinant DNA was named "pRCHuGF" and analyzed for nucleotide sequence using the Dideoxy method, revealing that it had the structure of FIG. 1. As shown in FIG. 1, the pRCHuGF had cDNA HuIGIF, containing the nucleotide sequence of SEQ ID NO:7 which encodes a precursor of the polypeptide, ligated to the downstream of a cytomegalovirus promotor, PCMV.

A seed culture of CHO-K1 cells (ATCC CCL61) from chinese hamster's ovary was inoculated into Ham's F12 medium (pH 7.2) supplemented with 10 v/v % fetal calf serum and incubated for proliferation. Thereafter, the proliferated cells were collected, washed with phosphate buffered saline (hereinafter abbreviated as "PBS") and suspended in PBS to give a cell density of $1\times10^7$ cells/ml. 0.8 ml of the suspension and 10 µg of the recombinant DNA pRCHuGF were placed in a cuvette, and the mixture was ice-chilled for 10 min, set to "GENE PULSER™", an apparatus of electroporation commercialized by Japan Bio-Rad Laboratories, Tokyo, Japan, and charged once with a discharged pulse, followed by promptly removing the cuvette and ice-chilling it for 10 min. Thereafter, the cell suspension was recovered from the cuvette, inoculated into Ham's F12 medium (pH 7.2) supplemented with 10 v/v % fetal calf serum, incubated in a 5 v/v % $CO_2$ incubator at 37° C. for 3 days, then admixed with G418 to give a final concentration of 400 µg/ml and incubated for 3 days under the same conditions as above. Forty-eight colonies were selected from about 100 colonies, and some of the selected ones were inoculated into a culture plate distributed with Ham's F12 medium (pH 7.2) supplemented with 10 v/v % fetal calf serum, and cultured for a week similarly as above. Thereafter, the cells in each well in the plate were lysed by adding to each well 10 mM Tris-HCl buffer (pH 8.5) containing 5.1 mM magnesium chloride, 0.5 w/v % deoxycholic acid, one w/v % "NONIDET P-40", a surfactant, 10 µg/ml aprotinin and 0.1 w/v % SDS.

Fifty µl aliquots of the resulting cell-lysate product were placed in containers, followed by adding 50 µl glycerol and dithiothreitol in an amount which gave a final concentration of 2 w/v % to the containers and allowing to stand the containers at 37° C. for one hour. Thereafter, the polypeptide in the cell-lysate was separated by SDS-polyacrylamide gel electrophoresis, and the polypeptide separated in the gel was in a conventional manner transferred to a nitrocellulose membrane, soaked for one hour in a previously obtained culture supernatant of a hybridoma, H-1 strain, which produces a monoclonal antibody specific to the polypeptide as disclosed in Japanese Patent Kokai No.231,598/96 applied by the same applicant of the present invention, and washed with 20 mM Tris-HCl buffer (pH 7.5) containing 0.05 v/v % tween 20 to remove an excessive amount of the monoclonal antibody. The nitrocellulose membrane was soaked for one hour in PBS containing rabbit antimouse immunoglobulin antibody labelled with horseradish peroxidase, washed with 50 mM Tris-HCl buffer (pH 7.5) containing 0.05 v/v % tween 20, and colored by soaking in 50 mM Tris-HCl buffer (pH 7.5) containing 0.005 v/v % hydrogen peroxide and 0.3 mg/ml diamino benzidine. Based on the coloration degree, a transformant clone, which more produced a precursor of the polypeptide, was selected and named "RCHuGF".

The transformant RCHuGF was inoculated into square culture flasks, into which were distributed Ham's F12 medium (pH 7.2) supplemented with 400 µg/ml G418 and 10 v/v % fetal calf serum, and incubated in a 5 v/v % $CO_2$ incubator at 37° C. for one week while replacing the medium with a fresh one on demand. Thereafter, an adequate amount of "TRYPSIN-EDTA", a trypsin commercialized by GIBCO Laboratories, Div. of Life Technologies, Inc., New York, USA, to detach the cells adhered to the walls of the flasks, and the detached cells were washed with PBS, further washed with ice-chilled 20 mM Hepes buffer (pH 7.4) containing 10 mM potassium chloride, 1.5 mM magnesium chloride and 0.1 mM ethylenediamine-N,N,N',N'-tetraacetic acid disodium salt, and allowed to stand for 20 min in 3-time volumes of a fresh preparation of the same buffer. Then, the cells were disrupted in a conventional manner, centrifuged at 10,000×g for 30 min to obtain a supernatant containing a precursor of the polypeptide. The precursor gave a molecular weight of about 24,000 daltons on SDS-polyacrylamide gel electrophoresis and had the amino acid sequence of SEQ ID NO:1 at the N-terminal region.

EXAMPLE 4-2

Conversion of Precursor

A substrate solution was prepared by dissolving the precursor of the polypeptide in Example 4-1 in 100 mM Hepes buffer (pH 7.4), containing 10 v/v % glycerol, 0.1 w/v % CHAPS and 2 mM dithiothreitol, to give a concentration of 500 nM, and mixed with 350 units/ml of the enzyme solution in Example 1, followed by the incubation at 37° C. At 0 min, 10 min, 30 min, one hour, 3 hours, 6 hours and 18 hours after initiating the incubation, a portion of the reaction mixture was sampled at each sampling time and admixed with iodoacetamide to give a final concentration of 200 µg/ml to suspend the reaction. The Western Blotting method using the monoclonal antibody, as disclosed in Japanese Patent Application No.231,598/96 applied by the same applicant of the present invention, was applied to the reaction mixture to study the change on passage of time during the conversion of the precursor into the active form.

The content of the active polypeptide in each sample collected at each sampling time was estimated by a bioassay using KG-1 cells (ATCC CCL246), a mononuclear cell line from a human acute myelocytic leukemia. The bioassay was as follows: KG-1 cells were suspended in RPMI 1640 medium (pH 7.4) supplemented with 10 v/v % fetal calf serum to give a cell density of $1.5\times10^6$ cells/ml, and the cell suspension was distributed to a 96-well microplate in an amount of 0.1 ml/well. To the microplate was added the above reaction mixture after diluted with RPMI 1640 medium (pH 7.4), supplemented with 10 v/v % fetal calf serum, in a volume of 0.1 ml/well, followed by incubating the microplate in a 5 v/v % $CO_2$ incubator at 37° C. for 24 hours. After completion of the incubation, 0.1 ml aliquots of the supernatants in the microplate's wells were sampled and quantified for IFN-γ using conventional enzyme immunoassay. The results were in Table 1. The IFN-γ content in Table 1 was expressed after converted into international units with respect to an IFN-γ standard, Gg23-901-530, obtained from the National Institutes of Health (NIH), USA.

TABLE 1

| Reaction time (min) | IFN-γ content (IU/ml) |
| --- | --- |
| 0 min | 280 |
| 10 min | 750 |
| 30 min | 1,000 |
| 1 hour | 1,800 |
| 3 hours | 3,100 |
| 6 hours | 3,900 |
| 18 hours | 4,200 |

Figure 2:
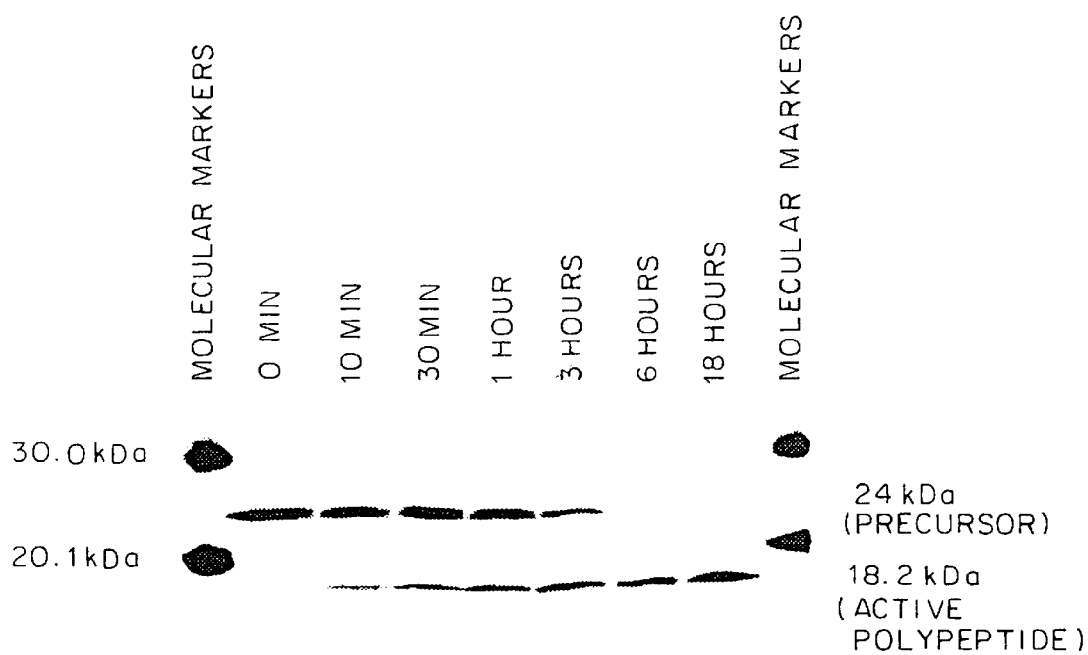
FIG. 2 is a visualized intermediate picture, displayed on a screen, of a gel electrophoresis pattern by the Western Blotting, which shows the change on passage of time during the conversion of a precursor of the present polypeptide into the active form.

As shown in the Western Blotting of FIG. 2, under this reaction conditions, a protein band with a molecular weight of about 24,000 daltons, corresponding to the precursor, gradually disappeared up to 3 hours after the initiation of the reaction, while a band with a molecular weight of about 18,200 daltons appeared. The IFN-γ content in Table 1 well agreed with the results; the producibility of IFN-γ as a reaction product gradually increased as a band with a molecular weight of about 18,200 daltons, corresponding to the active polypeptide. These results indicate that the present enzyme acted on a precursor of the polypeptide to convert the precursor into the active form which induces IFN-γ production in immunocompetent cells.

EXAMPLE 4-3

Physicochemical Properties of Active Polypeptide

EXAMPLE 4-3(a)

Purification of Active Polypeptide

The reaction mixture after an 18 hours' incubation in Example 4-2 was dialyzed against 10 mM phosphate buffer (pH 6.8), fed to a column of "DEAE 5PW", a gel for ion-exchange chromatography commercialized by Tosoh Corporation, Tokyo, Japan, which had been equilibrated with 10 mM phosphate buffer (pH 6.8), and fed with a linear gradient buffer of sodium chloride increasing from 0M to 0.5M in 10 mM phosphate buffer (pH 6.8), followed by collecting fractions eluted at sodium chloride concentrations of about 0.2–0.3M.

The fractions were pooled, dialyzed against PBS and fed to a column which had been prepared by providing a gel for immunoaffinity chromatography using a monoclonal antibody according to the method in Japanese Patent Application No.231,598/96 applied by the same applicant of the present invention, injecting the gel into a plastic cylindrical column, and washing the column with PBS. The column was fed with 100 mM glycine-HCl buffer (pH 2.5) to collect fractions containing the active form which induces IFN-γ production in immunocompetent cells. The fractions were pooled, dialyzed against sterilized distilled water, concentrated with a membrane filter, and lyophilized to obtain a purified active polypeptide in a solid form.

EXAMPLE 4-3(b)

Molecular Weight of Polypeptide

In accordance with the method as reported by U. K. Lemuli in Nature, Vol.227, pp.680–685 (1970), the purified polypeptide in Example 4-3(a) was electrophoresed in a polyacrylamide gel in the presence of 2 w/v % dithiothreitol as a reducing agent to show a major band in a position corresponding to about 18,000–19,500 daltons. The data shows that the present enzyme acted on a precursor of the polypeptide with a molecular weight of about 24,000 daltons to convert the precursor into the active form with a molecular weight lower than that of the precursor. The molecular markers used in this experiment were calf serum albumin with a molecular weight of 67,000 daltons, ovalbumin with a molecular weight of 45,000, carbonic acid anhydrase with a molecular weight of 30,000 daltons, soy bean trypsin inhibitor with a molecular weight of 20,100 daltons, and α-lactalbumin with a molecular weight of 14,400 daltons.

EXAMPLE 4-3(c)

Amino Acid Sequence of Polypeptide at the N-terminal Region

A conventional analysis using "MODEL 473", a protein sequencer commercialized by Applied Biosystems, Inc., Foster City, USA, revealed that the active polypeptide in Example 4-3(a) had the amino acid sequences of SEQ ID NO:3 at the N-terminal region. The data indicates that the present enzyme acted on a precursor of the polypeptide to cleave the polypeptide linkage between the aspartic acid 36 and tyrosine 37.

EXAMPLE 5

Activity of Inhibitory Agent on Enzyme

In the conversion method for precursor in Example 4-2, the present enzyme in Example 1 was admixed with 5 μM Ac-YVAD-CHO or 650 μM iodoacetamide and reacted at 37° C. for 3 hours. Each reaction mixture was separated on SDS-PAGE using 15 w/v % gel in the presence of 2 w/v % dithiothreitol, and analyzed on the Western Blotting method using a monoclonal antibody as disclosed in Japanese Patent Kokai No.231,598/96, revealing that no band corresponding to the active form was detected in each gel. This indicates that Ac-YVAD-CHO and iodoacetamide acted on the present enzyme as activity inhibitory agents.

EXAMPLE 6

Preparation of Enzyme

U-937 cells (ATCC CRL1593.2), a myelomonocytic cell line from a human histiocytic lymphoma, were suspended in RPMI 1640 medium which was contained in an about 10-ml plastic cylindrical diffusion chamber equipped with a membrane filter with a pore size of 0.5 μ. The chamber was intraperitoneally embedded in an adult rat which was then fed in a conventional manner for 4 weeks, then the chamber was removed from the rat. From the chamber, the proliferated cells were collected and washed with PBS and disrupted similarly as in Example 1, followed by purifying the mixture to obtain the present enzyme in a yield of about 5 units per rat.

EXAMPLE 7

Preparation of Enzyme

HL-60 cells (ATCC CCL240), a myelomonocytic cell line from a human promyelocytic leukemia, were suspended in RPMI 1640 medium (pH 7.2) supplemented with 10 v/v % fetal calf serum to give a cell density of about $3 \times 10^5$ cells/ml, and incubated in a 5 v/v % $CO_2$ incubator at 37° C. for 3 weeks while replacing with a fresh preparation of the same medium. From the culture, the proliferated cells were collected, washed with PBS and homogenized similarly as in Example 1, followed by purifying the resultant to obtain the present enzyme in a yield of about 30 units per L of the culture.

Analysis of the physicochemical properties of the enzyme thus obtained by the methods in Examples 2–5 revealed that the enzyme showed the same enzyme activity, molecular weight, and partial amino acid sequence as the one in Example 1, and the enzyme activity was inhibited by Ac-YVAD-CHO and iodoacetamide.

As described above, the present invention was made based on the finding of an enzyme which converts a precursor of a polypeptide, that induces IFN-γ production in immunocompetent cells, into the active form. The present enzyme with such an activity enables the production of the active form, which received similar processings as in human cells, is obtained by (i) contacting the enzyme with either cells which inherently produce the polypeptide or a precursor of the polypeptide produced from mammalian host cells which had been transformed by introducing a DNA encoding the polypeptide, or (ii) introducing both a DNA encoding the enzyme and a DNA encoding the polypeptide into mammalian host cells to express both the DNAs. This enzyme can be produced in a desired amount by the present method using cells as the sources.

The present invention having these useful functions and activities would be a significant invention that strongly contributes to this field.

While there has been described what is at present considered to be the preferred embodiments of the invention, it will be understood the various modifications may be made therein, and it is intended to cover in the appended claims all such modifications as fall within the true spirit and scope of the invention.

---

We claim:

1. An enzyme which converts a precursor of a polypeptide that induces interferon-γ production in an immunocompetent cell into the active form.

2. The enzyme of claim 1, which cleaves the linkage between the aspartic acid 36 and tyrosine 37 in SEQ ID NO:1 being contained in whole or in part by said precursor at the N-terminal region;

SEQ ID NO:1:

| Met 1 | Ala | Ala | Glu | Pro 5 | Val | Glu | Asp | Asn | Cys 10 | Ile | Asn | Phe | Val | Ala 15 | Met |
|---|---|---|---|---|---|---|---|---|---|---|---|---|---|---|---|
| Lys | Phe | Ile | Asp 20 | Asn | Thr | Leu | Tyr | Phe 25 | Ile | Ala | Glu | Asp | Asp 30 | Glu | Asn |
| Leu | Glu | Ser 35 | Asp | Tyr | Phe | Gly | Lys 40 | Leu. | | | | | | | |

3. The enzyme of claim 1, which acts on said precursor with the amino acid sequence of SEQ ID NO:2, where the symbol "Xaa" is "isoleucine" or "threonine", to convert it into the active form with the amino acid sequence of SEQ ID NO:3 at the N-terminal region;

SEQ ID NO:2:

| Met -35 | Ala | Ala | Glu | Pro | Val | Glu -30 | Asp | Asn | Cys | Ile | Asn -25 | Phe | Val | Aa | Met |
|---|---|---|---|---|---|---|---|---|---|---|---|---|---|---|---|
| Lys -20 | Phe | Ile | Asp | Asn | Thr -15 | Leu | Tyr | Phe | Ile | Ala -10 | Glu | Asp | Asp | Glu | Asn -5 |
| Leu | Glu | Ser | Asp | Tyr 1 | Phe | Gly | Lys | Leu 5 | Glu | Ser | Lys | Leu | Ser 10 | Val | Ile |
| Arg | Asn | Leu 15 | Asn | Asp | Gln | Val | Leu 20 | Phe | Ile | Asp | Gln | Gly 25 | Asn | Arg | Pro |
| Leu | Phe 30 | Glu | Asp | Met | Thr | Asp 35 | Ser | Asp | Cys | Arg | Asp 40 | Asn | Ala | Pro | Arg |
| Thr 45 | Ile | Phe | Ile | Ile | Ser 50 | Met | Tyr | Lys | Asp | Ser 55 | Gln | Pro | Arg | Gly | Met 60 |
| Ala | Val | Thr | Ile | Ser 65 | Val | Lys | Cys | Glu | Lys 70 | Ile | Ser | Xaa | Leu | Ser 75 | Cys |
| Glu | Asn | Lys | Ile 80 | Ile | Ser | Phe | Lys | Glu 85 | Met | Asn | Pro | Pro | Asp 90 | Asn | Ile |
| Lys | Asp | Thr 95 | Lys | Ser | Asp | Ile | Ile 100 | Phe | Phe | Gln | Arg | Ser 105 | Val | Pro | Gly |
| His | Asp 110 | Asn | Lys | Met | Gln | Phe 115 | Glu | Ser | Ser | Ser | Tyr 120 | Glu | Gly | Tyr | Phe |
| Leu 125 | Ala | Cys | Glu | Lys | Glu 130 | Arg | Asp | Leu | Phe | Lys 135 | Leu | Ile | Leu | Lys | Lys 140 |
| Glu | Asp | Glu | Leu | Gly 145 | Asp | Arg | Ser | Ile | Met 150 | Phe | Thr | Val | Gln | Asn 155 | Glu |
| Asp | | | | | | | | | | | | | | | |

SEQ ID NO:3:

| Tyr 1 | Phe | Gly | Lys | Leu. 5 |
|---|---|---|---|---|

4. The enzyme of claim 1, which has the following physicochemical properties:

(1) Molecular weight

Exhibiting molecular weights of about 25,000 and about 10,000 daltons on SDS-polyacrylamide gel electrophoresis;

(2) Partial amino acid sequence

Having an amino acid sequence selected from the group consisting of SEQ ID NO:4, where the symbol "Xaa" is "asparagine" or "aspartic acid", and SEQ ID NO:5; and (3) Inhibitory agent Being inhibited by iodoacetamide and acetyl-L-tyrosyl-L-valyl-L-alanyl-L-aspart-1-al;

SEQ ID NO:4:

| Xaa 1 | Pro | Ala | Met | Pro 5 | Thr | Ser | Ser | Gly | Ser 10 | Glu | Gly | Asn | Val | Lys 15 | Leu |
|---|---|---|---|---|---|---|---|---|---|---|---|---|---|---|---|
| Cys | Ser | Leu | | | | | | | | | | | | | |

SEQ ID NO:5:

| Ala 1 | Ile | Lys | Lys | Ala 5 | His | Ile | Glu | Lys | Asp 10 | Phe | Ile | Ala | Phe. | | |

5. The enzyme of claim 1, which is obtainable from a human hematopoietic cell.

6. A protein as an enzyme which converts a precursor of a polypeptide that induces interferon-γ production in an immunocompetent cell into the active form, said protein having the following physicochemical properties:
(1) Action
Cleaving the linkage between the aspartic acid 36 and tyrosine 37 in SEQ ID NO:1 being contained in whole or in part by said precursor at the N-terminal region;
(2) Molecular weight
Exhibiting molecular weights of about 25,000 and about 10,000 daltons on SDS-polyacrylamide gel electrophoresis;
(3) Partial amino acid sequence
Having an amino acid sequence selected from the group consisting of SEQ ID NO:4, where the symbol "Xaa" is "asparagine" or "aspartic acid", and SEQ ID NO:5;
(4) Inhibitory agent
Being inhibited by acetyl-L-tyrosyl-L-valyl-L-alanyl-L-aspart-1-al and iodoacetamide; and
(5) Producing cell
Being obtainable from a human hematopoietic cell.

7. A process for producing the enzyme of claim 1, which comprises proliferating a cell capable of producing the enzyme, and collecting the produced enzyme from the proliferated cells.

8. The process of claim 7, wherein said cell is a human hematopoietic cell.

9. The process of claim 7, which comprises transplanting said cell to a non-human warm-blooded animal, and proliferating the cell while allowing said cell to receive the animal's body fluid.

10. The process of claim 9, wherein said animal is a rodent.

11. The process of claim 7, wherein said enzyme is collected by one or more techniques selected from the group consisting of salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing.

12. A process for producing the protein of claim 6, which comprises proliferating a cell capable of producing the protein, and collecting the produced protein from the proliferated cells.

13. The process of claim 12, wherein said cell is a human hematopoietic cell.

14. The process of claim 12, which comprises transplanting said cell to a non-human warm-blooded animal, and proliferating the cell while allowing said cell to receive the animal's body fluid.

15. The process of claim 14, wherein said animal is a rodent.

16. The process of claim 12, wherein said protein is collected by one or more techniques selected from the group consisting of salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing.

17. A conversion method for a polypeptide, which comprises contacting the enzyme of claim 1 with a precursor of a polypeptide that induces interferon-γ production in an immunocompetent cell to convert said precursor into the active form.

18. The conversion method of claim 17, wherein said precursor contains the amino acid sequence of SEQ ID NO:2 where the symbol "Xaa" is "isoleucine" or "threonine".

19. The conversion method of claim 17, wherein said active form contains the amino acid sequence of SEQ ID NO:3 at the N-terminal region.

20. The conversion method of claim 17, wherein said active form contains the amino acid sequence of SEQ ID NO:6 where the symbol "Xaa" is "isoleucine" or "threonine";

SEQ ID NO:6:

| Tyr 1 | Phe | Gly | Lys | Leu 5 | Glu | Ser | Lys | Leu | Ser 10 | Val | Ile | Arg | Asn | Leu 15 | Asn |
|---|---|---|---|---|---|---|---|---|---|---|---|---|---|---|---|
| Asp | Gln | Val | Leu 20 | Phe | Ile | Asp | Gln | Gly 25 | Asn | Arg | Pro | Leu | Phe 30 | Glu | Asp |
| Met | Thr | Asp 35 | Ser | Asp | Cys | Arg | Asp 40 | Asn | Ala | Pro | Arg | Thr 45 | Ile | Phe | Ile |
| Ile | Ser 50 | Met | Tyr | Lys | Asp | Ser 55 | Gln | Pro | Arg | Gly | Met 60 | Ala | Val | Thr | Ile |
| Ser 65 | Val | Lys | Cys | Glu | Lys 70 | Ile | Ser | Xaa | Leu | Ser 75 | Cys | Glu | Asn | Lys | Ile 80 |
| Ile | Ser | Phe | Lys | Glu 85 | Met | Asn | Pro | Pro | Asp 90 | Asn | Ile | Lys | Asp | Thr 95 | Lys |
| Ser | Asp | Ile | Ile 100 | Phe | Phe | Gln | Arg | Ser 105 | Val | Pro | Gly | His | Asp 110 | Asn | Lys |
| Met | Gln | Phe 115 | Glu | Ser | Ser | Ser | Tyr 120 | Glu | Gly | Tyr | Phe | Leu 125 | Ala | Cys | Glu |
| Lys | Glu 130 | Arg | Asp | Leu | Phe | Lys 135 | Leu | Ile | Leu | Lys | Lys 140 | Glu | Asp | Glu | Leu |
| Gly 145 | Asp | Arg | Ser | Ile | Met 150 | Phe | Thr | Val | Gln | Asn 155 | Glu | Asp. | | | |

21. A conversion method for a polypeptide, which comprises contacting the protein of claim 6 with a precursor of a polypeptide that induces interferon-γ production in an immunocompetent cell to convert said precursor into the active form.

22. The conversion method of claim 21, which cleaves the linkage between the aspartic acid 36 and tyrosine 37 in SEQ ID NO:1 being contained in whole or in part by said precursor at the N-terminal region.

23. The conversion method of claim 21, wherein said precursor contains the amino acid sequence of SEQ ID NO:2 where the symbol "Xaa" is "isoleucine" or "threonine".

24. The conversion method of claim 21 wherein said active form contains the amino acid sequence of SEQ ID NO:3 at the N-terminal region.

25. The conversion method of claim 21, wherein said active form contains the amino acid sequence of SEQ ID NO:6 where the symbol "Xaa" is "isoleucine" or "threonine".

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal fragment ( x i ) SEQUENCE DESCRIPTION:SEQ ID NO:1:

```
Met  Ala  Ala  Glu  Pro  Val  Glu  Asp  Asn  Cys  Ile  Asn  Phe  Val  Ala  Met
1                   5                        10                       15

Lys  Phe  Ile  Asp  Asn  Thr  Leu  Tyr  Phe  Ile  Ala  Glu  Asp  Asp  Glu  Asn
              20                      25                       30

Leu  Glu  Ser  Asp  Tyr  Phe  Gly  Lys  Leu
              35                      40
```

( 2 ) INFORMATION FOR SEQ ID NO:2:

( i ) SEQUENCE CHARACTERISTICS:
        ( A ) LENGTH: 193 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION:SEQ ID NO:2:

```
Met  Ala  Ala  Glu  Pro  Val  Glu  Asp  Asn  Cys  Ile  Asn  Phe  Val  Ala  Met
-35                  -30                      -25

Lys  Phe  Ile  Asp  Asn  Thr  Leu  Tyr  Phe  Ile  Ala  Glu  Asp  Asp  Glu  Asn
```

```
            -20                     -15                     -10                      -5
Leu  Glu  Ser  Asp  Tyr  Phe  Gly  Lys  Leu  Glu  Ser  Lys  Leu  Val  Ile
                     1                   5                   10

Arg  Asn  Leu  Asn  Asp  Gln  Val  Leu  Phe  Ile  Asp  Gln  Gly  Asn  Arg  Pro
          15                     20                       25

Leu  Phe  Glu  Asp  Met  Thr  Asp  Ser  Asp  Cys  Arg  Asp  Asn  Ala  Pro  Arg
          30                     35                       40

Thr  Ile  Phe  Ile  Ile  Ser  Met  Tyr  Lys  Asp  Ser  Gln  Pro  Arg  Gly  Met
45                            50                   55                          60

Ala  Val  Thr  Ile  Ser  Val  Lys  Cys  Glu  Lys  Ile  Ser  Xaa  Leu  Ser  Cys
                    65                       70                       75

Glu  Asn  Lys  Ile  Ile  Ser  Phe  Lys  Glu  Met  Asn  Pro  Pro  Asp  Asn  Ile
                80                      85                       90

Lys  Asp  Thr  Lys  Ser  Asp  Ile  Ile  Phe  Phe  Gln  Arg  Ser  Val  Pro  Gly
          95                       100                     105

His  Asp  Asn  Lys  Met  Gln  Phe  Glu  Ser  Ser  Ser  Tyr  Glu  Gly  Tyr  Phe
          110                     115                     120

Leu  Ala  Cys  Glu  Lys  Glu  Arg  Asp  Leu  Phe  Lys  Leu  Ile  Leu  Lys  Lys
125                      130                     135                          140

Glu  Asp  Glu  Leu  Gly  Asp  Arg  Ser  Ile  Met  Phe  Thr  Val  Gln  Asn  Glu
                145                      150                     155

Asp
```

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (v) FRAGMENT TYPE: N-terminal fragment (xi) SEQUENCE DESCRIPTION:SEQ ID NO:3:

```
Tyr  Phe  Gly  Lys  Leu
1                    5
```

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (v) FRAGMENT TYPE: N-terminal fragment (xi) SEQUENCE DESCRIPTION:SEQ ID NO:4:

```
Xaa  Pro  Ala  Met  Pro  Thr  Ser  Ser  Gly  Ser  Glu  Gly  Asn  Val  Lys  Leu
1                        5                       10                          15

Cys  Ser  Leu
```

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS: single
        (D) TOPOLOGY: linear ( i i ) MOLECULE TYPE: peptide ( v ) FRAGMENT TYPE: N-terminal fragment ( x i ) SEQUENCE DESCRIPTION:SEQ ID NO:5:

| Ala | Ile | Lys | Lys | Ala | His | Ile | Glu | Lys | Asp | Phe | Ile | Ala | Phe |
|-----|-----|-----|-----|-----|-----|-----|-----|-----|-----|-----|-----|-----|-----|
| 1 | | | | 5 | | | | | 10 | | | | |

( 2 ) INFORMATION FOR SEQ ID NO:6:

( i ) SEQUENCE CHARACTERISTICS:
        ( A ) LENGTH: 157 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION:SEQ ID NO:6:

| Tyr | Phe | Gly | Lys | Leu | Glu | Ser | Lys | Leu | Ser | Val | Ile | Arg | Asn | Leu | Asn |
|-----|-----|-----|-----|-----|-----|-----|-----|-----|-----|-----|-----|-----|-----|-----|-----|
| 1 | | | | 5 | | | | | 10 | | | | | 15 | |
| Asp | Gln | Val | Leu | Phe | Ile | Asp | Gln | Gly | Asn | Arg | Pro | Leu | Phe | Glu | Asp |
| | | | 20 | | | | 25 | | | | | 30 | | | |
| Met | Thr | Asp | Ser | Asp | Cys | Arg | Asp | Asn | Ala | Pro | Arg | Thr | Ile | Phe | Ile |
| | | 35 | | | | | 40 | | | | | 45 | | | |
| Ile | Ser | Met | Tyr | Lys | Asp | Ser | Gln | Pro | Arg | Gly | Met | Ala | Val | Thr | Ile |
| | 50 | | | | | 55 | | | | | 60 | | | | |
| Ser | Val | Lys | Cys | Glu | Lys | Ile | Ser | Xaa | Leu | Ser | Cys | Glu | Asn | Lys | Ile |
| 65 | | | | | 70 | | | | | 75 | | | | | 80 |
| Ile | Ser | Phe | Lys | Glu | Met | Asn | Pro | Pro | Asp | Asn | Ile | Lys | Asp | Thr | Lys |
| | | | | 85 | | | | | 90 | | | | | 95 | |
| Ser | Asp | Ile | Ile | Phe | Phe | Gln | Arg | Ser | Val | Pro | Gly | His | Asp | Asn | Lys |
| | | | 100 | | | | | 105 | | | | | 110 | | |
| Met | Gln | Phe | Glu | Ser | Ser | Ser | Tyr | Glu | Gly | Tyr | Phe | Leu | Ala | Cys | Glu |
| | | 115 | | | | | 120 | | | | | 125 | | | |
| Lys | Glu | Arg | Asp | Leu | Phe | Lys | Leu | Ile | Leu | Lys | Lys | Glu | Asp | Glu | Leu |
| | 130 | | | | | 135 | | | | | 140 | | | | |
| Gly | Asp | Arg | Ser | Ile | Met | Phe | Thr | Val | Gln | Asn | Glu | Asp | | | |
| 145 | | | | | 150 | | | | | 155 | | | | | |

( 2 ) INFORMATION FOR SEQ ID NO:7:

( i ) SEQUENCE CHARACTERISTICS:
        ( A ) LENGTH: 579 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: leader peptide
        ( B ) LOCATION: 1..108
        ( C ) IDENTIFICATION METHOD: S
        ( A ) NAME/KEY: mat peptide
        ( B ) LOCATION: 109..579
        ( C ) IDENTIFICATION METHOD: S ( x i ) SEQUENCE DESCRIPTION: SEQ ID NO:7:

| ATG | GCT | GCT | GAA | CCA | GTA | GAA | GAC | AAT | TGC | ATC | AAC | TTT | GTG | GCA | ATG | 48 |
|-----|-----|-----|-----|-----|-----|-----|-----|-----|-----|-----|-----|-----|-----|-----|-----|----|
| Met | Ala | Ala | Glu | Pro | Val | Glu | Asp | Asn | Cys | Ile | Asn | Phe | Val | Ala | Met | |
| | | -35 | | | | -30 | | | | | -25 | | | | | |

| AAA | TTT | ATT | GAC | AAT | ACG | CTT | TAC | TTT | ATA | GCT | GAA | GAT | GAT | GAA | AAC | 96 |
|-----|-----|-----|-----|-----|-----|-----|-----|-----|-----|-----|-----|-----|-----|-----|-----|----|
| Lys | Phe | Ile | Asp | Asn | Thr | Leu | Tyr | Phe | Ile | Ala | Glu | Asp | Asp | Glu | Asn | |

-continued

```
          -20                        -15                        -10                         -5
CTG  GAA  TCA  GAT  TAC  TTT  GGC  AAG  CTT  GAA  TCT  AAA  TTA  TCA  GTC  ATA              144
Leu  Glu  Ser  Asp  Tyr  Phe  Gly  Lys  Leu  Glu  Ser  Lys  Leu  Ser  Val  Ile
                    1              5                        10

AGA  AAT  TTG  AAT  GAC  CAA  GTT  CTC  TTC  ATT  GAC  CAA  GGA  AAT  CGG  CCT              192
Arg  Asn  Leu  Asn  Asp  Gln  Val  Leu  Phe  Ile  Asp  Gln  Gly  Asn  Arg  Pro
          15                       20                       25

CTA  TTT  GAA  GAT  ATG  ACT  GAT  TCT  GAC  TGT  AGA  GAT  AAT  GCA  CCC  CGG              240
Leu  Phe  Glu  Asp  Met  Thr  Asp  Ser  Asp  Cys  Arg  Asp  Asn  Ala  Pro  Arg
     30                       35                            40

ACC  ATA  TTT  ATT  ATA  AGT  ATG  TAT  AAA  GAT  AGC  CAG  CCT  AGA  GGT  ATG              288
Thr  Ile  Phe  Ile  Ile  Ser  Met  Tyr  Lys  Asp  Ser  Gln  Pro  Arg  Gly  Met
45                            50                           55                      60

GCT  GTA  ACT  ATC  TCT  GTG  AAG  TGT  GAG  AAA  ATT  TCA  AYT  CTC  TCC  TGT              336
Ala  Val  Thr  Ile  Ser  Val  Lys  Cys  Glu  Lys  Ile  Ser  Xaa  Leu  Ser  Cys
                    65                            70                      75

GAG  AAC  AAA  ATT  ATT  TCC  TTT  AAG  GAA  ATG  AAT  CCT  CCT  GAT  AAC  ATC              384
Glu  Asn  Lys  Ile  Ile  Ser  Phe  Lys  Glu  Met  Asn  Pro  Pro  Asp  Asn  Ile
               80                            85                      90

AAG  GAT  ACA  AAA  AGT  GAC  ATC  ATA  TTC  TTT  CAG  AGA  AGT  GTC  CCA  GGA              432
Lys  Asp  Thr  Lys  Ser  Asp  Ile  Ile  Phe  Phe  Gln  Arg  Ser  Val  Pro  Gly
          95                            100                      105

CAT  GAT  AAT  AAG  ATG  CAA  TTT  GAA  TCT  TCA  TCA  TAC  GAA  GGA  TAC  TTT              480
His  Asp  Asn  Lys  Met  Gln  Phe  Glu  Ser  Ser  Ser  Tyr  Glu  Gly  Tyr  Phe
     110                      115                           120

CTA  GCT  TGT  GAA  AAA  GAG  AGA  GAC  CTT  TTT  AAA  CTC  ATT  TTG  AAA  AAA              528
Leu  Ala  Cys  Glu  Lys  Glu  Arg  Asp  Leu  Phe  Lys  Leu  Ile  Leu  Lys  Lys
125                      130                      135                     140

GAG  GAT  GAA  TTG  GGG  GAT  AGA  TCT  ATA  ATG  TTC  ACT  GTT  CAA  AAC  GAA              576
Glu  Asp  Glu  Leu  Gly  Asp  Arg  Ser  Ile  Met  Phe  Thr  Val  Gln  Asn  Glu
                    145                           150                     155

GAC                                                                                          579
Asp
```

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
AAG  GCC  AGT  GTG  CTG  GGC  CTG  GAC  AGT  CAG  CAA  GG                     35
```

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
ACA  GCC  AGT  GTG  ATG  GCT  AGT  CTT  CGT  TTT  GAA  CAG                    36
```